United States Patent [19]

Rienhardt

[11] Patent Number: 5,685,195
[45] Date of Patent: Nov. 11, 1997

[54] CRANK ASSEMBLY FOR A SCREEN WIPER DRIVE OF AN AUTOMOTIVE VEHICLE

[75] Inventor: Hans Peter Rienhardt, Neckarsulm, Germany

[73] Assignee: ITT Automotive Europe GMbH, Frankfurt, Germany

[21] Appl. No.: 387,890

[22] PCT Filed: Jul. 23, 1993

[86] PCT No.: PCT/EP93/01960

§ 371 Date: Feb. 23, 1995

§ 102(e) Date: Feb. 23, 1995

[87] PCT Pub. No.: WO94/05531

PCT Pub. Date: Mar. 17, 1994

[30] Foreign Application Priority Data

Aug. 27, 1992 [DE] Germany ............................ 42 28 493.7

[51] Int. Cl.$^6$ .............................. F16H 21/40; B60S 1/24; F16B 7/00
[52] U.S. Cl. ............................ 74/42; 15/250.3; 15/250.31; 403/353
[58] Field of Search ..................... 15/250.3, 250.31; 74/42, 43; 403/353

[56] References Cited

U.S. PATENT DOCUMENTS

| 1,637,125 | 7/1927 | Nelson ............................ 403/353 |
| 3,262,038 | 7/1966 | Smith ............................ 318/265 |
| 3,462,179 | 8/1969 | Hinkle ........................... 403/353 X |
| 3,485,112 | 12/1969 | Goosmann ...................... 403/353 X |
| 4,263,821 | 4/1981 | Savage et al. ................... 74/42 X |

FOREIGN PATENT DOCUMENTS

| 209502 | 5/1984 | Germany ......................... 403/353 |
| 4101063 | 7/1992 | Germany ......................... 15/250.3 |
| 516232 | 12/1939 | United Kingdom ............ 15/250.3 |

OTHER PUBLICATIONS

International Search Report for Application No. PCT/EP93/01960 filed 23 Jul. 1993.

*Primary Examiner*—Allan D. Herrmann
*Attorney, Agent, or Firm*—J. Gordon Lewis; Thomas N. Twomey

[57] ABSTRACT

A crank mechanism of a driving assembly of a screen wiper for use with an automotive vehicle preferrably a lever and a tongue in communication therewith through a swivel joint, with the tongue are eccentrically hinged to an actuated gear wheel, in particular, a worm gear wheel and with the lever is connected or connectible in a non-rotating way to a wiper shaft. The tongue and the lever, in the practice of the invention, are pivotally interconnected through a bajonet-type connection such that the crank mechanism can be connected without tools. The assembled position enabling tongue and lever to be joined together differs from any possible rotary position taken by these two elements during operation.

9 Claims, 3 Drawing Sheets

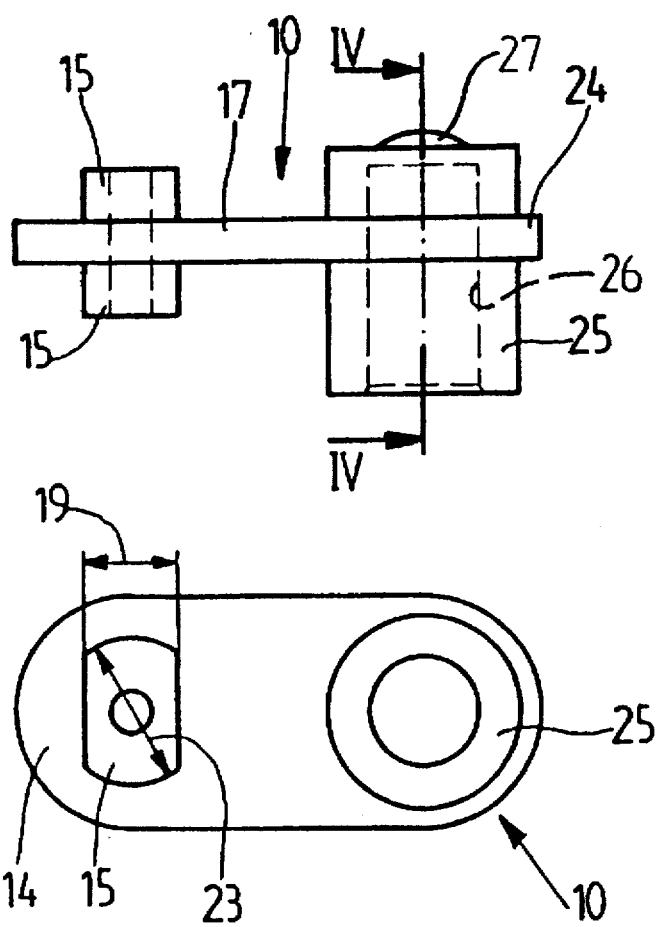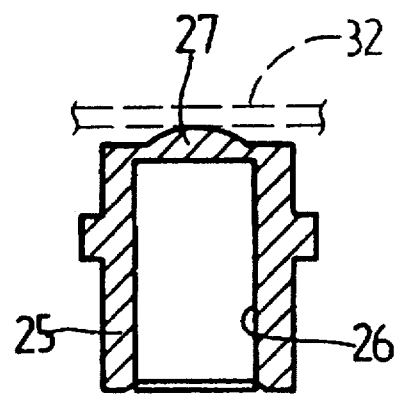

CRANK ASSEMBLY FOR A SCREEN WIPER DRIVE OF AN AUTOMOTIVE VEHICLE

TECHNICAL FIELD

The present invention crank mechanism and more particularly relates to crank mechanisms of windshield wiper drive linkages.

BACKGROUND OF THE INVENTION

Crank mechanisms are known wherein the lever and the tongue are interconnected through an articulated bolt separately produced and mounted which involves a relatively expensive and complex operation.

It is, therefore, an object of the invention to so improve the crank mechanism of the afore-mentioned type as to reduce the manufacturing costs, in particular, the costs of assembly.

According to the present invention two halves of a bayonet-type or twist-lock connection can be directly moulded to or formed on the tongue and the lever. They are connected in the relative position provided herefore to be subsequently placed in a position enabling assembly thereof on the driving arrangement and enclosing a different angle with respect to one another. This will be adequate to prevent an undesired unlocking of the bayonet-type connection from occurring. Because any desired relative position of the tongue and of the lever, during operation of the screen wiper arrangement, differs from the relative positions of these parts during establishing of the bayonet-type connection, this connection cannot unlock during operation of the screen wiper assembly. However, the afore-going conveys that this connection can be established with no need of using any tools or separate parts. This will reduce not only the number of parts but also the manufacturing costs and the time required for assembly. Compared with conventional designs, the parts number can be decreased from 9 to as low as 2.

According to a preferred form of embodiment the tongue and the lever, when in the coupled condition of assembly, are in approximately extended relationship with respect to one another, i.e. the knuckle joint during joining together of tongue and lever substantially are in the stretched position.

Preferrably the bayonet-type connection establishes a pivotal connection between lever and tongue, and corresponding steps will have to be taken to insure that the pivotal connection is prevented from axially unlocking. Such steps can be taken without incurring any special efforts in that the toggle moves within a chamber of the casing precluding any axial displacement of the entire knuckle joint or parts thereof in a direction transverse to the plane of movement.

Another embodiment of the invention is characterized in that the lever on the other end thereof is provided with a sleeve preferably including a blind bore for accommodating the inner end of the shaft. However, it is not imperative for the wiper shaft to be plugged or forced into the bore and blind bore, respectively, it can in stead also be injection-moulded.

Advantageously, a cambered supporting member inwardly supportable on a housing lid of the driving assembly is provided on the lever, arranged approximately opposite the sleeve. The supporting member prevents the movement of displacement of the lever in a direction transverse to the plane of movement thereof. In view of the cambered configuration, friction on the lid is minimized which especially applies if suitable pairs of substances are provided.

In another embodiment of the present the thickness of the tongue exceeds that of the lever at least in the area of connection. It goes without saying that the introduction slots referred to therein which are marginally open are arranged in congruent relationship. The advantage involved with this tongue configuration resides in that in no position of operation of the knuckle joint the tongue can separate from the lever, or vice-versa.

An enhanced simplification of the design, an additional decrease in costs and a further reduction of parts to 2 as mentioned before are attained through another embodiment of the invention in that a pivot pin for engagement with a bearing bore on the toothed gear, preferably worm gear wheel, is located on the end of the tongue facing away from the lever and protruding in the direction of the plane of movement thereof. Hence, in this instance, two parts are, indeed, adequate for this crank mechanism. The bearing pin will engage a bearing bore of the toothed gear with corresponding play. It is arranged, in known manner, eccentrically to the central bearing axis of the toothed gear.

Preferably, the lever and the tongue are made of plastic material, preferably by injection-moulding.

BRIEF DESCRIPTION OF THE DRAWINGS

FIG. 2 shows, in enlarged scale, a side view of the lever of the crank mechanism.

FIG. 3 is a plan view.

FIG. 4 is a sectional view of this lever along the line IV—IV of FIG. 2.

DETAILED DESCRIPTION OF THE PREERRED EMBODIMENT

Figure 1:
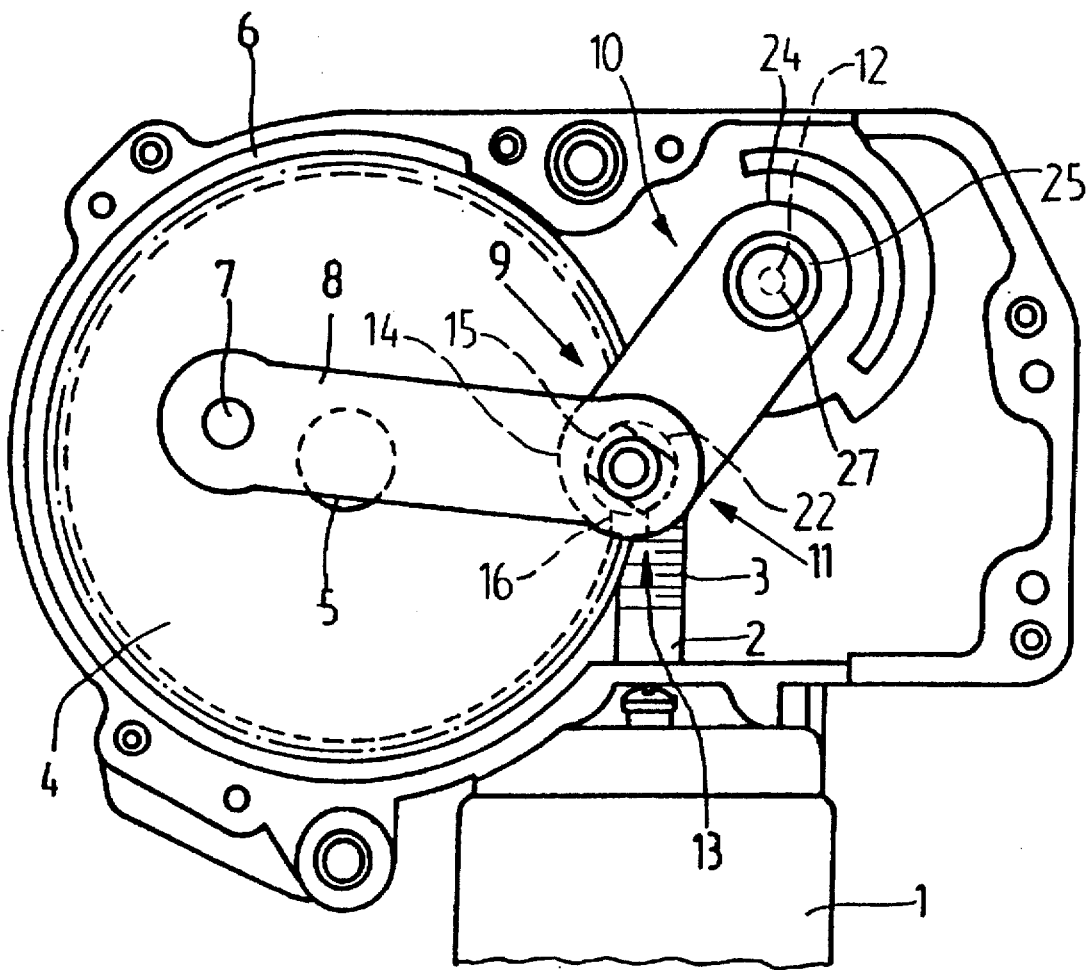
FIG. 1 is a plan view of the crank mechanism mounted into a driving assembly of a screen wiper for an automotive vehicle, with the crank housing being opened.
Figure 5:
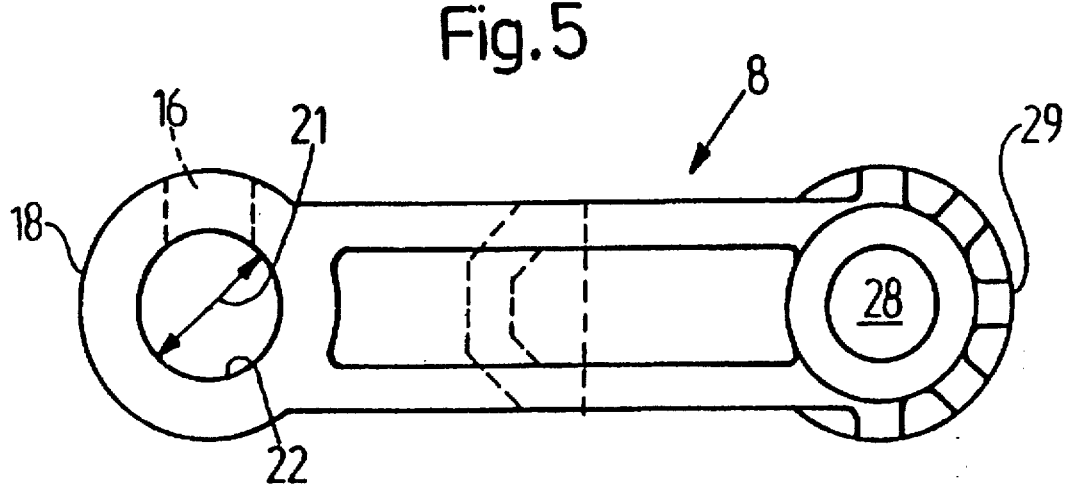
FIGS. 5 and 6 show the tongue according to FIGS. 2 and 3.

Now referring to FIG. 1, the driving shaft 2 of an electromotor 1 carries a worm 3 actuating a worm gear 4. Due to a shaft 5 the worm gear is rotatably disposed in the casing. A bearing pin 7 arranged eccentrically to the shaft 5 interconnects the gear wheel formed as the worm gear 4 and a tongue 8 of a crank mechanism 9. The latter includes a lever 10, with the two parts together forming a toggle as shown in FIG. 1. They are interconnected through a swivel joint 11 yet to be described in greater detail.

Located on the end of the lever 10 facing away from the swivel joint is a wiper shaft 12 traversing the casing 6 toward the outside and carrying, in known manner, the wiper arm on the free end thereof. For the sake of clearness, no lid 32 (shown in FIG. 4) covering the afore-mentioned elements of this screen wiper drive and partly locking the elements against a movement in a direction transverse to the image plane has been shown in FIG. 1.

In the practice of the invention, the tongue 8 and the lever 10 are pivotably interconnected by way of a bayonet-type connection 13, thereby enabling a connection to be established without resorting to any tools, with the said connection being prevented from automatically unlocking during operation due to the fact that the tongue 8 and the lever 10 can be interconnected only in an accurately predetermined position of assembly differing from any rotating position taken by the crank mechanism 9 during operation.

In this assembled position, according to the example of embodiment of the invention and in a special configuration thereof, the tongue 8 and the lever 10, in the coupled condition, are approximately in extended relationship with respect to one another. In other words, the tongue and the lever, initially, are aligned in parallel with respect to one another and then one of the two parts is displaced toward the second part in parallel to itself until a connecting pin 15 of an out-of-round cross-section as shown in FIG. 3 protruding on the one connecting end 14 of the lever 10 in a direction transverse to the plane of movement thereof is contained in an introduction slot 16 of the tongue 8 laterally open at the edge.

Figure 6:
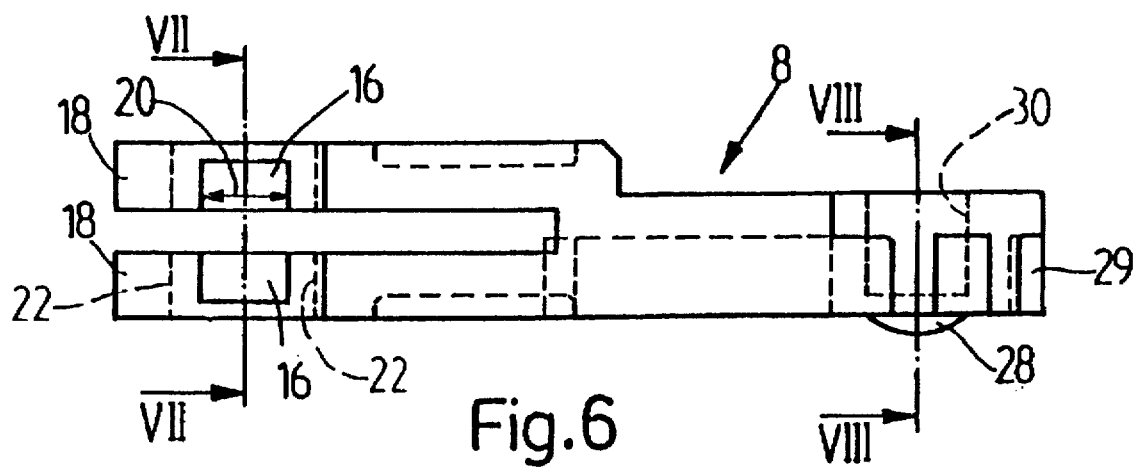

In the form of embodiment, the connection pin 15 protrudes on both sides beyond the basic member 17 of the lever 10. Consequently, also the introduction slot 16 is made up of two opposing slot parts (FIG. 6) which, in turn, are provided on a bifurcated end 18 of the tongue 5 forming an integral part of the swivel joint 11. According to FIG. 3, the connecting pin 15 has two parallel truncated sections, with the space therebetween determining the width 19 of the pin and corresponding to the slot width 20 (FIG. 6). Hence, the connecting pin 15 can be inserted into the slot 16 in a direction vertical to the image plane of FIG. 6, with the tongue 8 and the lever 10 assuming an extended position. Once this position has been changed by turning at least one of the two parts, the connecting pin 15 cannot be disengaged from the introduction slot 16 any longer which applies to all operating positions of the crank mechanism 9. However, in order to enable the connecting pin 15 to be rotated relative to the tongue 8, the diameter 21 of the bore 22 on the inner end of the introduction slot 16 corresponds to the diameter 23 of the connecting pin 15.

The lever 10 on the other end 24 thereof carries a sleeve 25. In the example of embodiment this sleeve is provided with a blind bore 26 accommodating, in a non-rotating way, the inner end of the afore-mentioned wiper shaft. A cambered support member 27 is quasi located on the bottom of the said blind bore 16. The support member 27, with the lid 32 mounted on the casing 6 (FIG. 1), is in abutment with an inner face of the lid 32, thereby causing an axial support of the lever 10.

Figures 7, 8A, 8B:
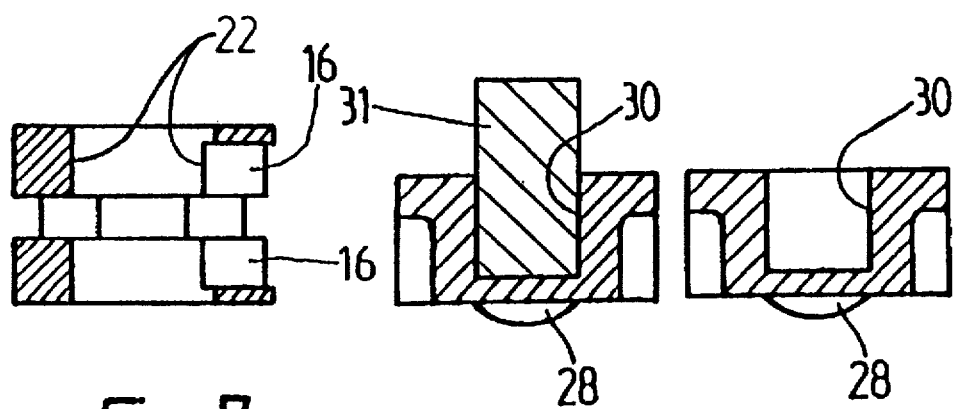
FIGS. 7 and 8A are sectional views along the lines VII—VII and VIII—VIII, respectively, of FIG. 6.
FIG. 8B is an alternative embodiment to that shown in FIG. 8A.

A cambered support member inwardly abutting or abuttable with the lid 32 is also provided on the wiper shaft end of the tongue to which it is preferably moulded which support member, in FIGS. 6 and 8, is designated by reference numeral 28.

In the present embodiment, a bore 30 (FIG. 8A) is provided for accommodating the bearing pin 7. Bore 30 is located on the end 29 of the tongue 8 facing away from the lever which bearing pin 7 connects the tongue 8 to the gear wheel and worm gear 4, respectively. In an alternative embodiment (shown in FIG. 8B), a pin 31 can be directly molded to the tongue 8. In this embodiment, pin 31 takes the place of bearing pin 7 of FIG. 1. This will be feasible, in particular, if the tongue 8 and the lever 10, preferably, are made of plastic material, in particular, plastic material which is injection molded.

I claim:

1. A crank mechanism of a driving assembly of a screen wiper for use with an automotive vehicle, comprising;

a lever and a tongue in communication therewith through a swivel joint, the tongue being eccentrically hinged to a worm gear wheel, wherein the lever is connected in a non-rotating way to a wiper shaft, wherein the tongue and the lever are pivotally interconnected through a bayonet-type connection, with the tongue and the lever, in the assembled position, taking a mutual rotary position which is different from each rotary position during operation.

2. A crank mechanism according to claim 1, wherein the tongue and the lever, in a coupled mounting condition, are approximately in extended relationship with respect to one another.

3. A crank mechanism according to claim 1 wherein the lever includes a connecting pin of an out-of-round cross-section projecting in a direction transverse to a plane of movement of the lever, and that the tongue on the associated connecting end comprises at least one introduction slot for the connecting pin, which is laterally open at the edge, with the connecting pin on the inner end thereof passing to a slot extension limited by a circular arc and forming a bearing bore and that an envelope of the connecting pin has a diameter corresponding to the one of the bearing bore.

4. A crank mechanism according to claim 3, wherein the lever includes a sleeve provided with a blind bore for accommodating the inner end of the wiper shaft.

5. A crank mechanism according to claim 4, wherein the driving assembly includes a cambered support member supported inwardly on a housing lid of the driving assembly.

6. A crank mechanism according to claim 3, wherein the tongue at its end connected to the lever is bifurcated into spikes, with the associated lever end gripping between the bifurcation spikes, and wherein provided on each bifurcation spike is an introduction slot.

7. A crank mechanism according to claim 6, wherein provided on the end of the tongue facing the wiper shaft is a cambered supporting member inwardly supportable on a housing lid.

8. A crank mechanism according to claim 7, wherein provided on the end of the tongue facing away from the lever is a bearing pin protruding in a direction transverse to the plane of movement thereof for engagement with a bearing bore on the worm gear wheel.

9. A crank mechanism according to claim 8, wherein the lever and the tongue are made from plastic material.

* * * * *